United States Patent
Sann

(10) Patent No.: US 7,820,690 B2
(45) Date of Patent: Oct. 26, 2010

(54) METHOD OF TREATING OR INHIBITING A NON-DIGESTIVE TRACT DERIVED ABDOMINAL DISORDER ASSOCIATED WITH PAIN USING A 5-HT, RECEPTOR ANTAGONIST

(75) Inventor: Holger Sann, Hannover (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 1016 days.

(21) Appl. No.: 11/080,546

(22) Filed: Mar. 16, 2005

(65) Prior Publication Data

US 2005/0209293 A1    Sep. 22, 2005

Related U.S. Application Data

(60) Provisional application No. 60/554,351, filed on Mar. 19, 2004.

(51) Int. Cl.
*A61K 31/437*    (2006.01)
(52) U.S. Cl. ...................................... 514/284
(58) Field of Classification Search ........................ None
See application file for complete search history.

(56) References Cited

U.S. PATENT DOCUMENTS

| 4,845,092 | A | 7/1989 | Sanger et al. | |
|---|---|---|---|---|
| 4,939,136 | A | 7/1990 | Haeck et al. | |
| 4,942,160 | A | 7/1990 | Sanger et al. | |
| 5,063,231 | A | 11/1991 | Sanger et al. | |
| 5,977,127 | A | 11/1999 | Bonnacker et al. | |
| 6,846,823 | B2 * | 1/2005 | Landau et al. | 514/249 |
| 7,048,906 | B2 * | 5/2006 | Lin et al. | 424/9.2 |
| 2004/0019101 | A1 | 1/2004 | Karlstadt et al. | |
| 2004/0138252 | A1 | 7/2004 | Ikeda et al. | |
| 2005/0070969 | A1 * | 3/2005 | Gerber | 607/40 |

FOREIGN PATENT DOCUMENTS

| EP | 0 279 512 A2 | 8/1988 |
|---|---|---|
| EP | 0 297 651 B1 | 1/1989 |
| EP | 0 467 365 A2 | 1/1992 |
| WO | WO 01/41748 A2 | 6/2001 |
| WO | WO 01/87305 A2 | 11/2001 |
| WO | WO 2004/089288 | 10/2004 |

OTHER PUBLICATIONS

"An Interview with GI Expert Emeran Mayer, MD" Interstital Cystitis association, Dec. 2000, http://www.ichelp.org/RelatedDiseases/ICAndGIDisturbances.html.*
Olden, KW., Clevelan Clinic Journal of Medicine, (Jun. 2003), 70, Suppl. 2, S3-S7.*
van de Merwe et al., International Journal of Urology, Oct. 2003, 10 Suppl. S35-38.*
Vippagunta et al., Advanced Drug Delivery Reviews, 48 (2001), pp. 3-26.*
A.C. Keung et al., Biopharmaceutics & Drug Disposition, 18(4), May 1997, 361-9.
G. Newsome, Journal of the Americal Academy of Nurse Practitioners, 15(2) (2003) 64-71.
Gillenwater et al., J. Urol., 140 (1988) 203-208.
J.C. Bryson, Seminars in Oncology, 19(6) suppl. 15, Dec. 1992, 26-32.
J.N. Krieger et al.,JAMA 282 (1999) 236-237.
Johansen et al., Current Opinion in Urology, Dec. 1, 2002 63-67.
K. Bouchelouche, J. Nordling, Curr.Opin.Urol., 2003; 13:309-13.
M. McNaughton-Collins et al., Ann. Intern. Med., 133 (2000) 367-381.
Maggi et al., J.Auton.Nerv.Sys.,38 (1992)201.
P. Toren et al., International Clinical Pharmacology, 14(6), Nov. 1999, 373-6.
Peeker and Fall, J. Urol., 167 (2002) 2470-2472.
R.M. Moldwin, Current Urology Reports 3/4 (2002) 313-318.
Z.H. Israili, Curr. Med. Chem.—CNS Agents 1 (2001) 171-199.
Ronald Wood et al., Automated Noninvasive Measurement of Cyclophosphamide-Induced Changes in Murine Voiding Frequency and Volume, *The Journal of Urology*, Feb. 2001, pp. 653-659, vol. 165, USA.
Pelvipharm webpage. Accessed Jun. 5, 2009. http://www.pelvipharm.com/index.php?id=49.

* cited by examiner

*Primary Examiner*—Phyllis G. Spivack
(74) *Attorney, Agent, or Firm*—Crowell & Moring LLP

(57) ABSTRACT

A method of treating or inhibiting non-digestive tract derived abdominal disorders associated with pain, in particular interstitial cystitis, chronic pelvic pain syndrome and/or abdominal pain associated with endometriosis, in a patient in need thereof, by administering to the patient a pharmaceutically effective amount of a 5-HT$_3$ receptor antagonist, in particular cilansetron, or a pharmacologically compatible derivative thereof, such as a salt and/or a solvates.

4 Claims, No Drawings

METHOD OF TREATING OR INHIBITING A NON-DIGESTIVE TRACT DERIVED ABDOMINAL DISORDER ASSOCIATED WITH PAIN USING A 5-HT, RECEPTOR ANTAGONIST

BACKGROUND OF THE INVENTION

The present invention relates to a novel medicinal use of 5-HT$_3$ receptor antagonists, in particular cilansetron, or their pharmacologically compatible derivatives, such as salts and/or solvates, for the treatment and/or inhibition of non-digestive tract derived abdominal disorders associated with pain, in particular interstitial cystitis, chronic pelvic pain syndrome and/or abdominal pain associated with endometriosis.

Regarding the therapeutic potential of 5-HT$_3$ receptor antagonists, it is already widely known that those can play a beneficial role in i.a. the treatment of gastrointestinal disorders (see e.g. Z. H. Israili, Curr. Med. Chem.—CNS Agents 1 (2001) 171-199 for a review).

The use of 5-HT$_3$ receptor antagonists for the treatment of urinary incontinence is already known from European patent publication no. EP 467,365.

Johansen et al. (see Current Opinion in Urology, 12/1 (2002) 63-67, cited as "Johansen et al." hereinafter) discuss a relation between the possible aetiological role of mast cells in interstitial cystitis and the importance of serotonin as a therapeutic agent in interstitial cystitis and chronic pelvic pain syndrome.

Of non-digestive tract derived abdominal disorders associated with pain, interstital cystitis, chronic pelvic pain syndrome and abdominal pain associated with endometriosis may best be cured by administration of 5-HT$_3$ receptor antagonists. Therapy of Interstitial Cystitis is preferred. According to the invention, "therapy" is meant to comprise either inhibition and/or treatment of a disorder.

Interstitial cystitis is a chronic disorder of the urinary bladder characterized by symptoms of urinary frequency and urgency, suprapubic pain, dyspareunia (anticipation of pain during sexual intercourse), nocturia and chronic pelvic pain (see e.g. G. Newsome, Journal of the American Academy of Nurse Practitioners, 15(2) (2003) 64-71). Interstitial cystitis occurs primarily in women, but also in men. Several pathophysiological mechanisms have been proposed in the past few years including epithelial dysfunction, activation of mast cells, neurogenic inflammation, autoimmunity, occult (viral or bacterial) infection, toxin exposure and pelvic floor dysfunction. Onset of interstitial cystitis is predominately in adulthood, although it does occur in childhood. The prevalence of interstitial cystitis has ranged from about 8 to about 60 cases per 100,000 female patients, depending on the population evaluated. About 10% of patients have severe symptoms that are associated with Hunner's ulcers on bladder biopsy. The rest could be grouped in those with or without bladder inflammation.

Interstitial cystitis in men is probably underdiagnosed and is most commonly misdiagnosed as prostatitis. Symptoms of Interstitial Cystitis are exacerbated by stress, certain foods and ovulatory hormones. Many patients also experience allergies, irritable bowel syndrome (IBS) and migraines. There have been various reports indicating dysfunction of the bladder glycosaminoglycan (GAG) protective layer and many publications showing a high number of activated bladder mast cells.

Diagnosis is by history, physical examination, laboratory tests, and cystoscopic examination. It thus largely remains a diagnosis of exclusion. Approved treatments to date include intravesical administration of dimethylsulfoxide (DMSO) or oral pentosanpolysulfate (PPS), but today's management of Interstitial Cystitis also may include dietary changes, antihistamines, tricyclic antidepressants, oral and intravesicle glucosaminoglycans, hydrodistention, pain management and emotional support. Criteria for diagnosis of interstitial cystitis have been established by the National Institute of Arthritis, Diabetes, Digestive and Kidney Diseases (Gillenwater et al. J. Urol 140 (1988) 203-208). These include glomerulations or Hunner's ulcer on cystoscopic examination and pain associated with bladder or urinary urgency. Recently, interstitial cystitis has frequently been divided into two subtypes: classical and nonulcer disease (Peeker and Fall, J. Urol. 167 (2002) 2470-2472).

Chronic pelvic pain syndrome is a syndrome often related to interstitial cystitis. According to the classification of the U.S. National Instituate of Health as "Type III Prostatitis" (see J. N. Krieger et al., JAMA 282 (1999) 236-237), it is regarded as a chronic, abacterial prostatitis. Patients with non-inflammatory chronic pelvic pain syndrome are the largest group of prostatitis patients according to the U.S. National Institute of Diabetes and Digestive and Kidney Diseases classification and are characterized by the absence of objective findings. Interestingly, for the majority of patients, no objective findings link the symptoms of prostatitis to the prostate gland or to the male genital tract. Thus, no findings seem to link the symptoms of chronic pelvic pain syndrome to the male in particular. Mounting evidence instead suggests that a significant overlap may exist between interstitial cystitis and chronic pelvic pain syndrome in epidemiology, pathophysiology and even therapy. In fact, both conditions might represent different manifestations of the same disease process. For example, very similar theories of pathogenesis exist for both conditions. Occult infections, epithelial dysfunction, neurogenic inflammation mast cell activation and autoimmunity are features that seem to play a role in the formation of interstital cystitis as well as in the formation of chronic pelvic pain syndrome (see e.g. Johansen et al.; R. M. Moldwin, Current Urology Reports 3/4 (2002) 313-318). Similar medications for both conditions will therefore seem promising. For a review on chronic pelvic pain syndrome see, for example, M. McNaughton-Collins et al., Ann. Intern. Med. 133 (2000) 367-381.

Endometriosis is a well-known gynecological disorder that affects 10 to 15% of women of reproductive age. It is a benign disease defined as the presence of viable uterine tissue, e.g. endometrial gland and stroma cells, outside the uterine cavity. It is most frequently found in the pelvic area, in particular in the ovaries. In women developing endometriosis, the endometrial cells entering the peritoneal cavity by retrograde menstruation (the most likely mechanism) have the capacity to adhere to and invade the peritoneal lining, and are then able to implant and grow. The implants respond to steroid hormones of the menstrual cycle in a way similar to the endometrium in the uterus. The infiltrating lesions and the blood from these lesions, which are unable to leave the body, cause inflammation of the surrounding tissue. The most common symptoms of endometriosis are dysmenorrhoea, dyspareunia and (chronic) abdominal pain. The occurrence of these symptoms is not related to the extent of the lesions. Some women with severe endometriosis are asymptomatic, while women with mild endometriosis may have severe pain. To date, no reliable and easy to use non-invasive test is available to diagnose endometriosis. Laparoscopy has to be performed to diagnose the disease. Endometriosis is classified according to the four stages established by the American Fertility Society (AFS). Stage I corresponds to minimal disease, while stage IV is severe, depending on the location and the extent of the endometriosis. Endometriosis is found in up to 50% of women with infertility. However, currently no causal relation has been proven between mild endometriosis and infertility. Moderate to severe endometriosis can cause tubal damage and adhesions leading to infertility. Despite extensive research, the cause of endometriosis is still largely unknown. Several theories for the origin of endometriosis have been proposed, although no single hypothesis explains all cases of the disease completely. However, the key event in all of these theories seems to be the occurrence of retrograde menstruation. The aims of treatment of endometriosis are currently pain relief, resolution of the endometriotic tissue, and restoration of fertility (if desired). The two common treatments are surgery or anti-inflammatory and/or hormonal therapy or a combination thereof.

SUMMARY OF THE INVENTION

It is an object of the present invention to provide a new method of treating and/or inhibiting non-digestive tract derived abdominal disorders associated with pain.

Another object of the invention is to provide a method of treating or inhibiting conditions such as interstitial cystitis, chronic pelvic pain syndrome or abdominal pain associated with endometriosis.

These and other object have been achieved in accordance with the present invention by providing a method of treating or inhibiting a non-digestive tract derived abdominal disorder associated with pain in a patient in need thereof, the method comprising administering to the patient a pharmaceutically effective amount of a $5\text{-}HT_3$ receptor antagonist or a pharmacologically compatible derivative thereof.

It has now surprisingly been discovered that $5\text{-}HT_3$ receptor antagonists can be used to treat and/or inhibit non-digestive tract derived abdominal disorders associated with pain, in particular interstitial cystitis, chronic pelvic pain syndrome and/or abdominal pain associated with endometriosis.

The invention thus relates to the use of a $5\text{-}HT_3$ receptor antagonist or a pharmacologically compatible derivative thereof, such as a salt and/or a solvate, for the treatment and/or inhibition of non-digestive tract derived abdominal disorders associated with pain, in particular interstitial cystitis, chronic pelvic pain syndrome and/or abdominal pain associated with endometriosis, in larger mammals and humans.

Examples of suitable $5\text{-}HT_3$ receptor antagonists which may be used according to the invention include, in particular, those selected from the group consisting of alosetron, azasetron, bemesetron, cilansetron, dolasetron, fabesetron, galdansetron, granisetron, indisetron, itasetron, lerisetron, lurosetron, ondansetron, palonosetron, ramosetron, ricasetron, tropisetron, zacopride and zatosetron.

Cilansetron is the preferred $5\text{-}HT_3$ receptor antagonist. Cilansetron falls within the scope of U.S. Pat. No. 4,939,136 (=EP 297,651) and has the chemical name (R)-(−)-4,5,6,8,9,10-hexahydro-10-[(2-methyl-1H-imidazol-1-yl)methyl]-11H-pyrido-[3,2,1-jk]-carbazol-11-one (alternative name: (10R)-5,6,9,10-tetrahydro-10-[(2-methyl-1H-imidazol-1-yl)methyl]-4H-pyrido[3,2,1-jk]carbazol-11(8H)-one). Cilansetron may advantageously be used in the form of its monohydrochloride. Usually, cilansetron monohydrochloride monohydrate is used. Other pharmacologically compatible acid addition salts of cilansetron are also known, for example, from U.S. Pat. No. 4,939,136, the disclosure of which is incorporated herein by reference.

The beneficial influence of $5\text{-}HT_3$ receptor antagonists according to the invention can be demonstrated e.g. by an in vivo animal test model predictive for the therapeutic potential of test compounds in non-digestive tract derived abdominal disorders associated with pain, in particular of interstitial cystitis. In this test model, the effect of $5\text{-}HT_3$ receptor antagonists on rats with cyclophosphamide-induced cystitis was investigated.

Inflammation of the bladder responsible for bladder overactivity was induced by an intraperitoneal (i.p.) cyclophosphamide injection (150 mg/kg, i.p.) 48 hours before testing (Maggi et al., J Auton Nerv Syst 38 (1992) 201) using male Wistar rats weighing 300-350 g. The rats were anesthetized with urethane delivered subcutaneously in saline (1.2 g/kg), and their temperature was maintained at 37° C. Following a midline abdominal incision, a catheter was inserted through the bladder dome and sealed with a tie. The catheter was connected via a T-tube to a pressure transducer and a syringe pump, to allow filling of the bladder with warm (37° C.) saline at 50 µl/min simultaneously with recording of intravesical pressure. This catheter was later used for cystometry.

For each voiding and non-voiding contraction, the threshold pressure (ThP, corresponding to the bladder pressure at the onset of the voiding contraction (mm Hg)), the maximal voiding pressure (MP, defined by the maximal bladder pressure reached during voiding contraction (mm Hg)) the basal pressure (BaP, defined by the lowest bladder pressure reached after the voiding contraction (mm Hg)) and the area under the curve of the bladder pressure (AUP) during voiding (mm Hg×s) was calculated for each rat and averaged for each condition. In addition, the frequency of contractions was determined.

Test groups consisting of 10 rats each were used. Drug treatments were carried out as described in the following Table 1.

TABLE 1

Group design for test model of $5\text{-}HT_3$ receptor antagonists on rats with cyclophosphamide-induced cystitis

| Group | Pretreatment 48 hours before acute treatment | Acute treatment |
| --- | --- | --- |
| 1 (control) | Vehicle | Vehicle |
| 2 (cystitis control) | Cyclophosphamide 150 mg/kg i.p. | Vehicle |
| 3 (cystitis + reference compound) | Cyclophosphamide 150 mg/kg i.p. | HOE140 130 µg/kg i.v. |
| 4 (cystitis + cilansetron 0.01 mg/kg i.v.) | Cyclophosphamide 150 mg/kg i.p. | Cilansetron 0.01 mg/kg i.v. |
| 5 (cystitis + cilansetron 0.1 mg/kg i.v.) | Cyclophosphamide 150 mg/kg i.p. | Cilansetron 0.1 mg/kg i.v. |

In groups 2 through 5, cystitis was induced by administration of cyclophosphamide 150 mg/kg intraperitoneally (i.p.) 48 hours before the experiment. Group 1 served as a control group. Drugs or vehicle to be tested were injected 10 minutes before the beginning of cystometry. Besides three doses of cilansetron (groups 4-5), HOE140 (D-Arginyl-[Hyp3, Thi5, D-Tic7, Oic8]-bradykinin), a bradykinin 2 receptor antagonist, was used as a reference standard known to be active in this model. During the cystometry the pressure changes due to transvesical perfusion of warm saline at 50 µl/min were recorded over 60 minutes. Parameters (as outlined above) were analyzed for each bladder filling.

Cyclophosphamide pretreatment consistently changed all parameters of cystometry but micturition pressure. Compared to the vehicle control group (group 1) the basal pressure, threshold pressure and frequency of bladder contraction in the cystitis group were consistently increased in the cystitis group (group 2) (see Table 2), whereas the area under the curve of the bladder contractions as well as the volume of perfusion at the onset of the first micturition was consistently decreased in the cystitis group (group 2) (see Table 2). Thus cystitis resulted in decreased bladder compliance (i.e. greater bladder pressures were reached with smaller volumes of perfusion) and bladder overactivity.

TABLE 2

Effects of test compounds in rats with cyclophosphamide-induced cystitis

|  | Group 1 vehicle control | group 2 Cyclo-phosphamide cystitis control | group 3 Cyclo-phosphamide cystitis + HOE140 | group 4 cyclo-phosphamide cystitis + cilansetron 0.01 mg/kg i.v. | group 5 cyclo-phosphamide cystitis + cilansetron 0.1 mg/kg i.v. |
| --- | --- | --- | --- | --- | --- |
| basal pressure [mmHg] | 13 | 19 | 16 | 16 | 14 |
| threshold pressure [mmHg] | 15 | 20 | 17 | 17 | 15 |
| frequency [hours$^{-1}$] | 15 | 35 | 30 | 26 | 28 |

Treatment with HOE140 decreased the cystitis induced changes basal pressure and threshold pressure, as well as frequency of bladder contractions by 50, 60 and 25%, respectively (see Tables 2 and 3). Micturition pressure area under the curve and first micturition volume were not affected by HOE140 treatment. It can be concluded that HOE140 partially alleviated some of the effects of cystitis as it changed key parameters of micturition towards values observed in the control group.

TABLE 3

Inhibition of cystitis effects

| | % inhibition of cystitis effects | | |
| --- | --- | --- | --- |
| | group 3 cyclophos-phamide cystitis + HOE140 | group 4 cyclophosphamide cystitis + cilansetron 0.01 mg/kg i.v. | group 5 cyclophosphamide cystitis + cilansetron 0.1 mg/kg i.v. |
| basal pressure | 50 | 50 | 83 |
| threshold pressure | 60 | 60 | 100 |
| frequency | 25 | 45 | 35 |

Treatment with cilansetron in a concentration as low as 0.01 mg/kg i.v. decreased cystitis induced changes in basal pressure and threshold pressure, as well as frequency of bladder contractions by 50, 60 and 45%, respectively (see Tables 2 and 3). Thus, it was similarly effective to, or even more effective than, the reference compound HOE 140. At 0.1 mg/kg i.v. cilansetron was even more potent in decreasing the cystitis evoked changes in basal pressure and threshold pressure by 83 and 100%, respectively (see Tables 2 and 3).

Acute treatment with HOE140 130 μg/kg reduced the symptoms of bladder overactivity associated with cyclophosphamide pretreatment. The dosing of 0.01 and 0.1 mg/kg cilansetron reduced these symptoms to an equivalent or slightly greater extent. Thus in the foregoing animal test model on cystometry in rats with cyclophosphamide-induced cystitis, cilansetron showed a beneficial effect superior to the effect caused by HOE140.

As therapeutic agents, the 5-HT$_3$ receptor antagonists or their pharmacologically compatible acid addition salts and/or their solvates may be administered in conventional pharmaceutical preparations. In an individual case, special dosage forms may be indicated. The doses to be used may vary individually and will naturally vary according to the type of condition to be treated and the substance used. In general, however, medicinal forms with an active substance content of 0.2 to 200 mg, in particular 1 to 50 mg, of active substance per individual dose are suitable for administration to humans and larger mammals. The compounds may be contained according to the invention, together with conventional pharmaceutical auxiliaries and/or carriers, in solid or liquid pharmaceutical preparations. Examples of solid preparations are preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of the active substances may contain the usual diluents, such as water, oils and/or suspension agents, such as polyethylene glycols and the like. Other auxiliaries may additionally be added, such as preservatives, taste correctives and the like.

A 5-HT$_3$ receptor antagonist or a pharmacologically compatible acid addition salt and/or a solvate thereof, preferably cilansetron, can be mixed and formulated with the pharmaceutical auxiliaries and/or carriers in known manner. For the production of solid medicament forms, cilansetron or its acid addition salt can, for example, be mixed with the auxiliaries and/or carriers in conventional manner and can be wet or dry granulated. The granules or powder can be poured directly into capsules or be pressed into tablet cores in conventional manner. These can be coated in known manner if desired.

The following example is intended to illustrate the production of pharmaceutical preparations containing cilansetron hydrochloride.

EXAMPLE I

Tablets Containing Cilansetron

| Composition: | |
| --- | --- |
| Cilansetron monohydrochloride monohydrate | 4 parts |
| Corn starch | 30 parts |
| Lactose | 70 parts |
| Polyvinylpyrrolidone (Kollidon 25 ™) | 5 parts |
| Magnesium stearate | 2 parts |
| Talcum | 3 parts |
| Total: | 114 parts |

Preparation Procedure:

The active substance was mixed with corn starch and fine-powdered lactose in a mixer. The resulting mixture was moistened thoroughly with a 20% solution of polyvinylpyrrolidone (Kollidon 25® by BASF) in demineralized water. If necessary, further demineralized water was added. The moist granules were passed through a 2 mm sieve, dried on trays at 40° C. and then passed through a 1 mm sieve (Frewitt machine). Once the granules had been mixed with magnesium stearate and talcum, tablets having a weight of 114 mg were pressed therefrom, so that each tablet contained 4 mg active substance.

Likewise or preferably, other pharmaceutical preparations of cilansetron may be used, for example stabilised pharmaceutical preparations known from U.S. Pat. No. 5,977,127 (=EP 895,782), the disclosure of which is incorporated herein by reference.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating or inhibiting a non-digestive tract derived abdominal disorder associated with pain selected from the group consisting of interstitial cystitis, chronic pelvic pain Syndrome and abdominal pain associated with endometriosis in a patient in need thereof, said method consisting essentially of administering to said patient a pharmaceutically effective amount of a 5-HT$_3$ receptor antagonist consisting essentially of cilansetron or a pharmacologically compatible acid addition salt thereof.

2. A method according to claim 1, wherein the abdominal disorder is interstitial cystitis.

3. A method according to claim 1, wherein the 5-HT$_3$ receptor antagonist consists essentially of cilansetron hydrochloride.

4. A method according to claim 1, wherein the 5-HT$_3$ receptor antagonist consists essentially of cilansetron hydrochloride monohydrate.

* * * * *